(12) United States Patent
Zuk et al.

(10) Patent No.: US 12,399,173 B2
(45) Date of Patent: Aug. 26, 2025

(54) METHOD FOR RE-USING TEST PROBE AND REAGENTS IN BIOCHEMICAL ASSAY BASED ON INTERFEROMETRY

(71) Applicant: Access Medical Systems, Ltd., Palo Alto, CA (US)

(72) Inventors: Robert F. Zuk, Menlo Park, CA (US); Pu Li, Los Altos, CA (US); Jackie Shek Kei Chan, Mountain View, CA (US); Indrani Chakraborty, Fremont, CA (US)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 482 days.

(21) Appl. No.: 17/754,473

(22) PCT Filed: Oct. 7, 2020

(86) PCT No.: PCT/US2020/054518
§ 371 (c)(1),
(2) Date: Apr. 1, 2022

(87) PCT Pub. No.: WO2021/071903
PCT Pub. Date: Apr. 15, 2021

(65) Prior Publication Data
US 2024/0044886 A1 Feb. 8, 2024

Related U.S. Application Data

(60) Provisional application No. 62/913,064, filed on Oct. 9, 2019.

(51) Int. Cl.
*B01L 3/00* (2006.01)
*B01F 33/302* (2022.01)
(Continued)

(52) U.S. Cl.
CPC ..... *G01N 33/54373* (2013.01); *G01N 33/557* (2013.01)

(58) Field of Classification Search
None
See application file for complete search history.

(56) References Cited

U.S. PATENT DOCUMENTS

| 12,055,486 B2 | 8/2024 | Tan |
| 2009/0068759 A1 | 3/2009 | Arenas et al. |

(Continued)

FOREIGN PATENT DOCUMENTS

| WO | 1993017335 A1 | 9/1993 |
| WO | 1995010043 A1 | 4/1995 |

(Continued)

OTHER PUBLICATIONS

European Patent Office (EPO), Extended European Search Report, EP No. 20875344.2, Sep. 5, 2023.

*Primary Examiner* — Jennifer Wecker
*Assistant Examiner* — Oyeleye Alexander Alabi
(74) *Attorney, Agent, or Firm* — Perkins Coie LLP; Viola T. Kung (57) ABSTRACT

The present invention is directed to biochemical assay methods, which re-use a hapten-immobilized test probe and reagents for quantitating an analyte or measuring kinetic binding in different samples, anywhere from about 3 to 20 times, while maintaining acceptable assay performance. The methods use a conjugate solution either comprising (i) an anti-hapten antibody and a capture antibody against an analyte, or (ii) an anti-hapten antibody and streptavidin, in each cycle and regenerate the hapten-coated test probe by dipping the test probe in an acidic solution having pH about 1-4, optionally further dipping in a DMSO solution, after the completion of each cycle of reaction. The robustness of the hapten-immobilized solid phase allows utilization of dena- (Continued)

turation reagents for efficient elution of the immune complexes after each cycle without compromising the binding activity of the hapten on the solid phase.

20 Claims, 7 Drawing Sheets

(51) Int. Cl.

| | | |
|---|---|---|
| B01F 33/3033 | (2022.01) | |
| B01L 7/00 | (2006.01) | |
| B01L 9/00 | (2006.01) | |
| B65G 47/80 | (2006.01) | |
| B82Y 20/00 | (2011.01) | |
| B82Y 30/00 | (2011.01) | |
| B82Y 40/00 | (2011.01) | |
| C12M 1/34 | (2006.01) | |
| C12M 3/06 | (2006.01) | |
| C12N 1/14 | (2006.01) | |
| C12N 1/20 | (2006.01) | |
| C12Q 1/02 | (2006.01) | |
| C12Q 1/6806 | (2018.01) | |
| C12Q 1/6844 | (2018.01) | |
| C12Q 1/6848 | (2018.01) | |
| C12Q 1/686 | (2018.01) | |
| G01N 15/10 | (2024.01) | |
| G01N 15/14 | (2024.01) | |
| G01N 15/1433 | (2024.01) | |
| G01N 21/29 | (2006.01) | |
| G01N 21/65 | (2006.01) | |
| G01N 33/543 | (2006.01) | |
| G01N 33/557 | (2006.01) | |
| G01N 33/574 | (2006.01) | |
| G01N 33/58 | (2006.01) | |

(56) References Cited

U.S. PATENT DOCUMENTS

| | | |
|---|---|---|
| 2017/0052178 A1 | 2/2017 | Zuk et al. |
| 2018/0180606 A1* | 6/2018 | Zuk .................. G01N 33/54306 |
| 2019/0250154 A1 | 8/2019 | Zuk et al. |

FOREIGN PATENT DOCUMENTS

| | | | |
|---|---|---|---|
| WO | 1996022533 A1 | 7/1996 | |
| WO | 2009033056 A1 | 3/2009 | |
| WO | 2018071523 A1 | 4/2018 | |
| WO | 2018081646 A1 | 5/2018 | |
| WO | WO-2019105916 A1 * | 6/2019 | ............ G01N 33/53 |
| WO | 2020206175 A1 | 8/2020 | |

* cited by examiner

| Probe Position | Known concentration (ug/ml) | Calculated concentration (ug/ml) | | | | | | | | SD | AVG | % CV | |
| --- | --- | --- | --- | --- | --- | --- | --- | --- | --- | --- | --- | --- | --- |
| 1 | 700 | 785 | 894 | 853 | 908 | 862 | 786 | 806 | 760 | 756 | 770 | 56.57443 | 818 | 6.9 |
| 2 | 500 | 393 | 397 | 406 | 396 | 426 | 437 | 445 | 467 | 467 | 468 | 30.16713 | 429.5 | 7.02 |
| 3 | 300 | 358 | 334 | 332 | 331 | 345 | 375 | 347 | 351 | 351 | 352 | 13.61739 | 348.1 | 3.91 |
| 4 | 100 | 92 | 100.4 | 99.9 | 101 | 92.9 | 90.4 | 91 | 91 | 91 | 89.9 | 4.637109 | 93.85 | 4.99 |
| 5 | 30 | 30 | 29.9 | 30.1 | 20.6 | 28.15 | 28 | 28.3 | 28.11 | 28.11 | 28.4 | 0.915134 | 28.856 | 3.13 |
| 6 | 10 | 12 | 9.8 | 9.8 | 9.9 | 11.3 | 11.3 | 11.4 | 11.5 | 11.5 | 11.5 | 0.810007 | 10.95 | 7.33 |
| 7 | 3 | 3.5 | 3.04 | 3.02 | 3.02 | 2.77 | 2.8 | 2.78 | 2.79 | 2.79 | 2.7 | 0.237816 | 2.923 | 8.14 |
| 8 | 1 | 1 | 1 | 1 | 1 | 1 | 1 | 1 | 1 | 1 | 1 | 0 | 1 | 0 |

| Probe Position | Known concentration (ug/ml) | Binding Rate | | | | | | | | | |
| --- | --- | --- | --- | --- | --- | --- | --- | --- | --- | --- | --- |
| 1 | 700 | 0.88 | 0.89 | 0.88 | 0.86 | 0.86 | 0.84 | 0.86 | 0.84 | 0.83 | 0.86 |
| 2 | 500 | 0.69 | 0.68 | 0.67 | 0.67 | 0.66 | 0.67 | 0.68 | 0.7 | 0.68 | 0.71 |
| 3 | 300 | 0.66 | 0.63 | 0.61 | 0.62 | 0.61 | 0.63 | 0.61 | 0.62 | 0.61 | 0.62 |
| 4 | 100 | 0.3 | 0.3 | 0.3 | 0.29 | 0.29 | 0.28 | 0.288 | 0.29 | 0.28 | 0.28 |
| 5 | 30 | 0.11 | 0.11 | 0.11 | 0.11 | 0.1 | 0.1 | 0.107 | 0.1063 | 0.1 | 0.1072 |
| 6 | 10 | 0.04 | 0.04 | 0.038 | 0.038 | 0.038 | 0.038 | 0.038 | 0.038 | 0.038 | 0.038 |
| 7 | 3 | 0.012 | 0.012 | 0.0125 | 0.0125 | 0.007 | 0.0067 | 0.0066 | 0.0065 | 0.0066 | 0.0065 |
| 8 | 1 | 0.004 | 0.004 | 0.004 | 0.004 | 0.004 | 0.0039 | 0.0039 | 0.0037 | 0.0037 | 0.0036 |

| Probe Position | Known concentration (ug/ml) | | | | | | | | | |
| --- | --- | --- | --- | --- | --- | --- | --- | --- | --- | --- |
| 1 | 700 | | | | | | | | | |
| 2 | 500 | | | | | | | | | |
| 3 | 300 | | | | | | | | | |
| 4 | 100 | 1.96 | 1.97 | 1.99 | 2.02 | 2.06 | 2.06 | 2.08 | 2.13 | 2.23 | 2.22 |
| 5 | 30 | | | | | | | | | |
| 6 | 10 | | | | | | | | | |
| 7 | 3 | | | | | | | | | |
| 8 | 1 | | | | | | | | | |

FIG. 9

Association-CRP     Dissociation no CRP

METHOD FOR RE-USING TEST PROBE AND
REAGENTS IN BIOCHEMICAL ASSAY
BASED ON INTERFEROMETRY

This application is a National Stage of International Application PCT/US2020/054518, filed Oct. 7, 2020; which claims the priority of U.S. Provisional Application No. 62/913,064, filed Oct. 9, 2019. The contents of the above-identified applications are incorporated herein by reference in their entireties.

FIELD OF THE INVENTION

The present invention related to a biochemical assay based on interferometry. The method uses a dual antibody conjugate solution in each cycle and regenerates the hapten-coated test probe by dipping the test probe in an acidic solution having pH about 1-4, after the completion of each cycle of reaction. The method re-uses a hapten-immobilized test probe and reagents for quantitating an analyte in different samples, from about 2 to 15 times.

BACKGROUND OF THE INVENTION

Label free detection methods such as bio-layer interferometry (BLI) and surface plasmon resonance (SPR) have become standard methods in the study of receptor/ligand binding in biomedical research and in the development of therapeutics. Throughout the healthcare industry, including research applications and drug development, cost containment is a major issue. The expense of label free sensors limits their application, and consequently, limits the potential contributions of label free sensors in research and development.

Typical approaches to reducing the cost of immunoassays entail minimizing manufacturing expenses for materials, labor, and facilities overhead.

Any method to recycle immune reagents typically centers upon disassociating the immune complex with a denaturing agent such as an acidic/basic pH solution, organic solvents, chaotropic agents, etc. However, the denaturation step often changes the antibody charge, hydration, hydrogen bonding and tertiary structure where it no longer binds to antigen. Exposing the antibody back to the initial binding conditions close to physiologic pH and ionic strength, is hoped to restore original binding activity, however, few antibodies can tolerate repeated exposures to denaturation conditions without adversely impacting some aspect of their binding properties and consequently, assay performance.

There is a need for reducing the cost of immunoassays, while maintaining the assay performance at the same time.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within ±10% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

An "aspect ratio" of a shape refers to the ratio of its longer dimension to its shorter dimension.

A "binding molecule," refers to a molecule that is capable to bind another molecule of interest.

"A binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, lectin and carbohydrates. Preferred binding pairs are biotin and streptavidin, biotin and avidin, fluorescein and anti-fluorescein, digioxigenin/anti-digioxigenin.

A "bispecific antibody" is an antibody that can simultaneously bind to two different types of antigen.

"Immobilized," as used herein, refers to reagents being fixed to a solid surface. When a reagent is immobilized to a solid surface, it is either be non-covalently bound or covalently bound to the surface.

"A monolithic substrate," as used herein, refers to a single piece of a solid material such as glass, quartz, or plastic that has one refractive index.

A "probe," as used herein, refers to a monolithic substrate having as aspect ratio (length-to-width) of at least 2 to 1 with a thin-film layer coated on the sensing side. A probe has a distal end and a proximal end. The proximal end (also refers to probe tip in the application) has a sensing surface coated with a thin layer of analyte-binding molecules.

A "waveguide" refers to a device (e.g., a duct, coaxial cable, or optic fiber) designed to confine and direct the propagation of electromagnetic waves (as light).

The present invention discloses a method to re-use a biochemical assay test probe and reagents, from about 2 to 15 times, while maintaining acceptable assay performance, in a bio-layer interferometry (BLI) assay for quantitation or for kinetics. The present invention re-uses test probe and reagents and saves the cost on a per test basis.

There are several key elements to practice the invention. The first feature of this invention is that the solid phase (probe) is coated with a hapten. Haptens, commonly defined as small organic molecules less than about 1500 Daltons, that are antigenic, but with very poor immunogenicity. Consequently, haptens have to be linked to a larger polymer, typically proteins, in order to generate anti hapten antibodies. Haptens have their antibody binding based on their primary chemical structure, and there is no conformation dependence in its antibody binding. Hapten antigens therefore retain their antibody binding property even after repeated steps that denature anti-hapten antibodies and immunocomplexes. The present invention uses a hapten-immobilized test probe and an anti-hapten antibody which binds to the hapten-coated solid phase; the immune complex is subsequently disassociated with a denaturation reagent. Subsequently re-immersing the hapten-coated solid phase in a reagent with anti-hapten antibody restores the original amount of anti-hapten antibody to bound on the solid phase. The hapten coated solid phase can be subjected to multiple cycles of denaturation followed by anti-hapten antibody binding. The robustness of the hapten-coated solid phase allows utilization of multiple denaturation reagents for efficient elution of the immune complexes.

Suitable haptens for the present invention include, for example, small organic molecules such as nitrotyrosine, dinitrophenol, trinitrophenol, nitrophenol, and aminobenzoic acid; dyes such as Alexa Fluor, cyanine dyes, TRITC, Lucifer Yellow, Texas Red, and boron-dipyrromethene (Bodipy); peptides such as Myc, Flag, and polyhistidine; drugs such as theophylline, phenytoin, phenobarbital, valproic acid, penicillin, and gentamycin; steroids such as progesterone, testosterone, and estradiol, and vitamins such as biotin and Vitamin D. Preferred haptens are fluorescein, biotin, and digoxigenin.

The second feature of the invention entails chemically conjugating the anti-hapten to member of a binding pair. Such binding pairs could be antibody/antigen, receptor/ligand, or oligonucleotides with complementary sequences. For example, the anti-hapten antibody is conjugated with a capture antibody that binds to a specific analyte in a sample. The hapten probe/anti-hapten-binding member format can be applied to a multitude of binding assays.

The probe of the present invention is regenerated and recycled, while a fresh anti-hapten/member of a binding pair is captured on the probe at each cycle, thereby maintaining the assay performance.

The third feature of the invention is bio-layer interferometry (BLI) detection of the binding of the second member of the binding pair to the probe surface. BLI detection is advantageous because labels are not required that could alter the binding between the binding pair. A denaturation step to elute the complexes from the probe surface is then performed and the probe is cycled back to the anti-hapten/binding member conjugate. Since a fresh coating of the anti-hapten/binding member is used at each cycle, assay performance is maintained.

Other features of the invention include a small diameter probe (≤5 mm). Due of its small surface area, the probe consumes a negligible amount of the anti-hapten/binding member reagent allowing its reuse in subsequent cycles. The robustness of the hapten coated solid phase allows utilization of a variety of denaturation reagents for efficient elution of the complexes.

Biosensor Interferometer Systems

Figure 1A:
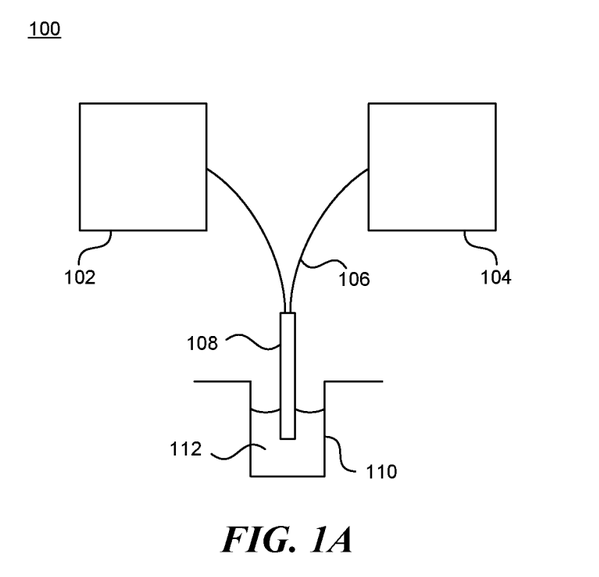
FIG. 1A depicts a biosensor interferometer that includes a light source, a detector, a waveguide, and an optical assembly (also referred to as a "probe").
Figure 1B:
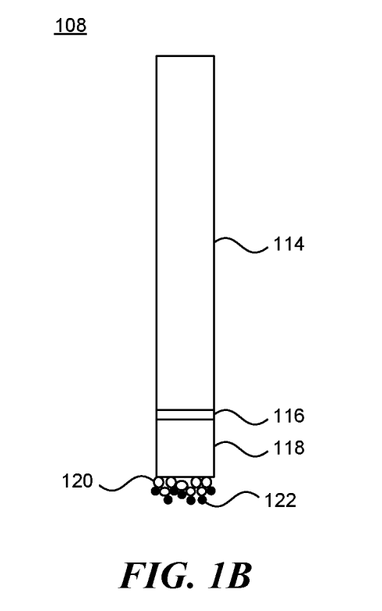
FIG. 1B depicts an example of a conventional probe.

The present invention is suitable for several biosensor interferometer systems. FIGS. 1A-B illustrate one example of such a system. FIG. 1A depicts a biosensor interferometer 100 (or simply "interferometer") that includes a light source 102, a detector 104, a waveguide 106, and an optical assembly 108 (also referred to as a "probe"). The probe 108 may be connected to the waveguide 106 via a coupling medium.

The light source 102 may emit white light that is guided toward the probe 108 by the waveguide 106. For example, the light source 102 may be a light-emitting diode (LED) that is configured to produce light over a range of at least 50 nanometers (nm), 100 nm, or 150 nm within a given spectrum (e.g., 400 nm or less to 700 nm or greater). Alternatively, the interferometer 100 may employ a plurality of light sources having different characteristic wavelengths, such as LEDs designed to emit light at different wavelengths in the visible range. The same function could be achieved by a single light source with suitable filters for directing light with different wavelengths onto the probe 108.

The detector 104 is preferably a spectrometer, such as an Ocean Optics USB4000, that is capable of recording the spectrum of interfering light received from the probe 108. Alternatively, if the light source 102 operates to direct different wavelengths onto the probe 108, then the detector 104 can be a simple photodetector capable of recording intensity at each wavelength. In another embodiment, the detector 104 can include multiple filters that permit detection of intensity at each of multiple wavelengths.

The waveguide 106 can be configured to transport light emitted by the light source 102 to the probe 108, and then transport light reflected by surfaces within the probe 108 to the detector 104. In some embodiments the waveguide 106 is a bundle of optical fibers (e.g., single-mode fiber optic cables), while in other embodiments the waveguide 106 is a multi-mode fiber optic cable.

As shown in FIG. 1B, the probe 108 includes a monolithic substrate 114, a thin-film layer (also referred to as an "interference layer"), and a biomolecular layer (also referred to as a "biolayer") comprised of analyte molecules 122 that have bound to analyte-binding molecules 120. The monolithic substrate 114 is comprised of a transparent material through which light can travel. The interference layer is also comprised of a transparent material. When light is shone on the probe 108, the proximal surface of the interference layer may act as a first reflecting surface and the biolayer may act as a second reflecting surface. As further described below, light reflected by the first and second reflecting surfaces may form an interference pattern that can be monitored by the interferometer 100.

The interference layer normally includes multiple layers that are combined in such a manner to improve the detectability of the interference pattern. Here, for example, the interference layer is comprised of a tantalum pentoxide ($Ta_2O_5$) layer 116 and a silicon dioxide ($SiO2$) layer 118. The tantalum pentoxide layer 116 may be thin (e.g., on the order of 10-40 nm) since its main purpose is to improve reflectivity at the proximal surface of the interference layer. Meanwhile, the silicon dioxide layer 118 may be comparatively thick (e.g., on the order of 650-900 nm) since its main purpose is to increase the distance between the first and second reflecting surfaces.

To perform a test, the probe 108 can be suspended in a microwell 110 (or simply "well") that includes a sample 112. Analyte molecules 122 will bind to the analyte-binding molecules 120 along the distal end of the probe 108 over the course of the diagnostic test, and these binding events will result in an interference pattern that can be observed by the detector 104. The interferometer 100 can monitor the thickness of the biolayer formed along the distal end of the probe 108 by detecting shifts in a phase characteristic of the interference pattern.

Figure 2:
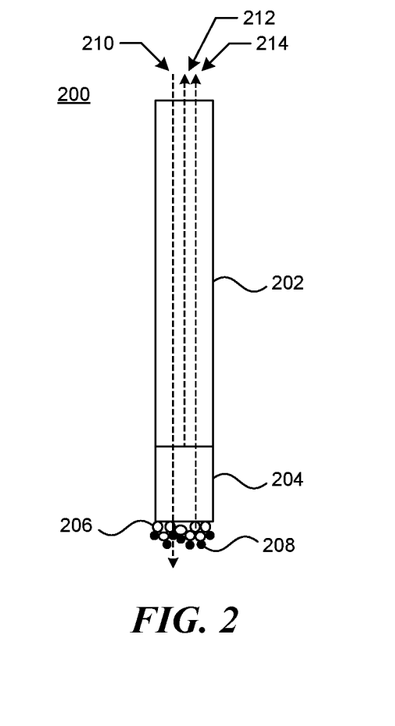
FIG. 2 depicts another configuration of a probe.

FIG. 2 illustrates another biosensor interferometer probe. The probe includes a monolithic substrate that has a first and a second surfaces arranged substantially parallel to one another at opposite ends of the monolithic substrate, an interference layer coated on the second surface of the monolithic substrate, and a layer of analyte-binding molecules coated on the interference layer. The interference layer will generally be comprised of magnesium fluoride (MgF2). A first interface between the monolithic substrate and the interference layer acts as a first reflecting surface when light is shone on the interferometric sensor, while a second interface between a biolayer formed by analyte molecules in a sample binding to the analyte-binding molecules and a solution containing the sample acts as a second reflecting surface when the light is shone on the probe. As described above, the thickness of the biolayer can be estimated based on the interference pattern of light reflected by the first and second reflecting surfaces.

The probe 200 includes an interference layer 204 that is secured along the distal end of a monolithic substrate 202. Analyte-binding molecules 206 can be deposited along the distal surface of the interference layer 204. Over the course of a biochemical test, a biolayer will form as analyte molecules 208 in a sample bind to the analyte-binding molecules 206.

As shown in FIG. 2, the monolithic substrate 202 has a proximal surface (also referred to as a "coupling side") that can be coupled to, for example, a waveguide of an interferometer and a distal surface (also referred to as a "sensing side") on which additional layers are deposited. Generally, the monolithic substrate 202 has a length of at least 3 millimeters (mm), 5 mm, 10 mm, or 15 mm. In a preferred embodiment, the aspect ratio (length-to-width) of the monolithic substrate 202 is at least 5 to 1. In such embodiments, the monolithic substrate 202 may be said to have a columnar form. The cross section of the monolithic substrate 202 may a circle, oval, square, rectangle, triangle, pentagon, etc. The monolithic substrate 202 preferably has a refractive index that is substantially higher than the refractive index of the interference layer 204, such that the proximal surface of the interference layer 204 effectively reflects light directed onto the probe 200. The preferred refractive index of the monolithic substrate may be higher than 1.5, 1.8, or 2.0. Accordingly, the monolithic substrate 202 may be comprised of a high-refractive-index material such as glass (refractive index of 2.0) rather than a low-refractive-index material such as quartz (refractive index of 1.46) or plastic (refractive index of 1.32-1.49).

The interference layer 204 is comprised of at least one transparent material that is coated on the distal surface of the monolithic substrate 202. These transparent material(s) are deposited on the distal surface of the monolithic substrate 202 in the form of thin films ranging in thickness from fractions of a nanometer (e.g., a monolayer) to several micrometers. The interference layer 204 may have a thickness of at least 500 nm, 700 nm, or 900 nm. An exemplary thickness is between 500-5,000 nm (and preferably 800-1, 200 nm). Here, for example, the interference layer 204 has a thickness of approximately 900-1,000 nm, or 940 nm.

In contrast to conventional probes, the interference layer 204 has a substantially similar refractive index as the biolayer. This ensures that the reflection from the distal end of the probe 200 is predominantly due to the analyte molecules 208 rather than the interface between the interference layer 204 and the analyte-binding molecules 206. In some embodiments the interference layer 204 is comprised of magnesium fluoride ($MgF_2$), while in other embodiments the interference layer 204 is comprised of potassium fluoride (KF), lithium fluoride (LiF), sodium fluoride (NaF), lithium calcium aluminum fluoride ($LiCaAlF_6$), sodium aluminum fluoride ($Na3AlF_6$), strontium fluoride ($SrF_2$), aluminum fluoride ($AlF_3$), sulphur hexafluoride ($SF_6$), etc. Magnesium fluoride has a refractive index of 1.38, which is substantially identical to the refractive index of the biolayer formed along the distal end of the probe 200. For comparison, the interference layer of conventional probes is normally comprised of silicon dioxide, and the refractive index of silicon dioxide is approximately 1.4-1.5 in the visible range. Because the interference layer 204 and biolayer have similar refractive indexes, light will experience minimal scattering as it travels from the interference layer 204 into the biolayer and then returns from the biolayer into the interference layer 204.

In one embodiment, the probe 200 includes an adhesion layer that is deposited along the distal surface of the interference layer 204 affixed to the monolithic substrate 202. The adhesion layer may be comprised of a material that promotes adhesion of the analyte-binding molecules 206. One example of such a material is silicon dioxide. The adhesion layer is generally very thin in comparison to the interference layer 204, so its impact on light traveling toward, or returning from, the biolayer will be minimal. For example, the adhesion layer 310 may have a thickness of approximately 3-10 nm, while the interference layer 304 may have a thickness of approximately 800-1,000 nm. The biolayer formed by the analyte-binding molecules 306 and analyte molecules 308 will normally have a thickness of several nm.

When light is shone on the probe 200, the proximal surface of the interference layer 204 may act as a first reflecting surface and the distal surface of the biolayer may act as a second reflecting surface. The presence, concentration, or binding rate of analyte molecules 208 to the probe 200 can be estimated based on the interference of beams of light reflected by these two reflecting surfaces. As analyte molecules 208 attach to (or detach from) the analyte-binding molecules 206, the distance between the first and second reflecting surfaces will change. Because the dimensions of all other components in the probe 200 remain the same, the interference pattern formed by the light reflected by the first and second reflecting surfaces is phase shifted in accordance with changes in biolayer thickness due to binding events.

In operation, an incident light signal 210 emitted by a light source is transported through the monolithic substrate 202 toward the biolayer. Within the probe 200, light will be reflected at the first reflecting surface resulting in a first reflected light signal 212. Light will also be reflected at the second reflecting surface resulting in a second reflected light signal 214. The second reflecting surface initially corresponds to the interface between the analyte-binding molecules 206 and the sample in which the probe 200 is immersed. As binding occurs during the biochemical test, the second reflecting surface becomes the interface between the analyte molecules 208 and the sample.

Figure 3A:
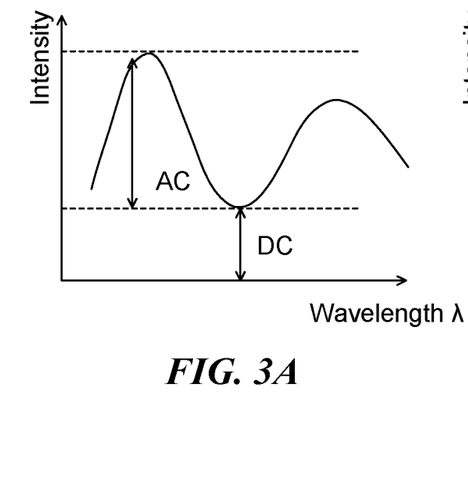
FIGS. 3A-3B illustrate the principles of detection in a thin-film interferometer.
Figure 3B:
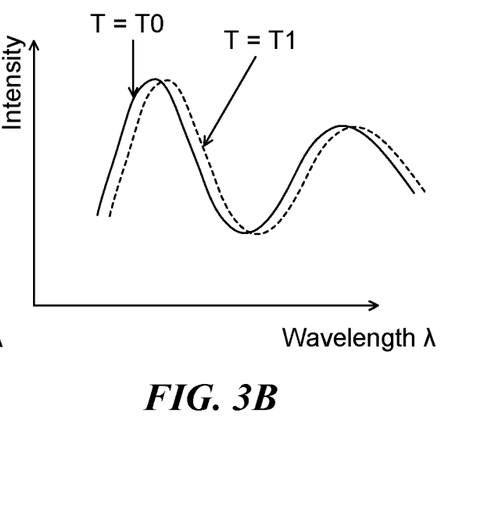

The first and second reflected light signals 212, 214 form a spectral interference pattern, as shown in FIG. 3A. When analyte molecules 208 bind to the analyte-binding molecules 206 on the distal surface of the interference layer 204, the optical path of the second reflected light signal 214 will lengthen. As a result, the spectral interference pattern shifts from T0 to T1 as shown in FIG. 3B. By measuring the phase shift continuously in real time, a kinetic binding curve can be plotted as the amount of shift versus the time. The association rate of an analyte molecule to an analyte-binding molecule immobilized on the distal surface of the interference layer 204 can be used to calculate analyte concentration in the sample. Hence, the measure of the phase shift is the detection principle of a thin-film interferometer.

Recycling Protocols for Biochemical Assays

The present invention is directed to a biochemical assay, using the same hapten-coated test probe and the same reagents for different samples. The test probe is regenerated by acidic treatment, optionally by further DMSO treatment.

First Embodiment—Quantitation

Figure 4:
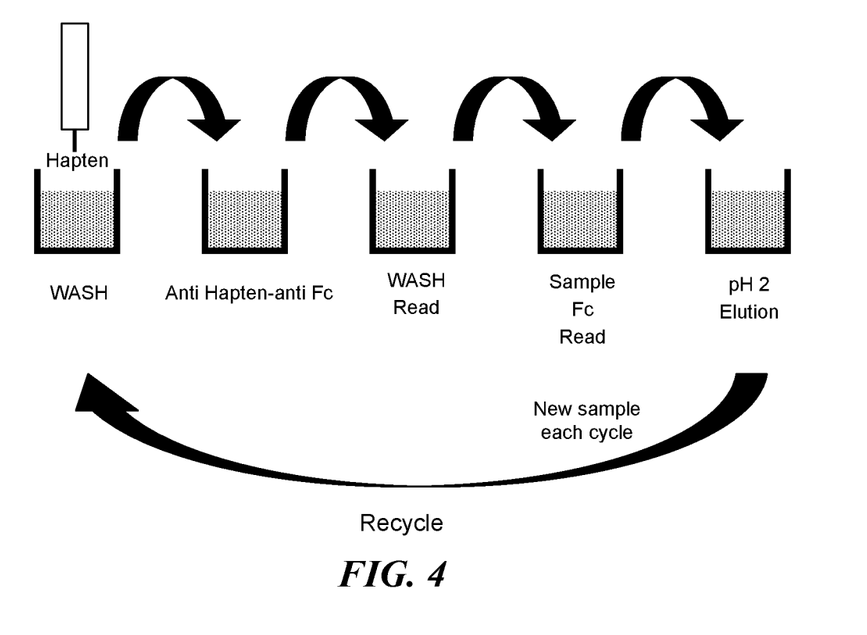
FIG. 4 illustrates the first embodiment of the invention for antigen quantitation, where the anti-hapten antibody is covalently linked to a capture antibody.

In a first embodiment, the method detects an analyte in multiple samples. This embodiment is illustrated in FIG. 4 with Fc as the analyte in the sample to be quantitated.

The method comprises the steps of: (a) obtaining a probe having a hapten immobilized on the tip of the probe, wherein the diameter of the tip surface is ≤5 mm; (b) dipping the probe tip in a dual antibody vessel containing a dual antibody solution comprising an anti-hapten antibody covalently linked to a capture antibody, wherein the capture antibody is an antibody against an analyte; (c) dipping the probe tip in a first wash vessel comprising a first aqueous solution for a first period of time to determine a baseline interferometry pattern of the probe tip; (d) dipping the probe tip into a sample vessel containing a liquid sample having the analyte for a second period of time to determine a second interferometry pattern of the immunocomplex formed at the probe tip; (e) determining the analyte concentration in the sample by measuring the interferometry phase shift between the second interferometry pattern and the baseline interferometry pattern, and quantitating the phase shift against a calibration curve; (f) dipping the probe tip in an acidic solution having pH about 1.0-4.0 to elute the immunocomplex from the probe tip; (g) dipping the probe tip in a second wash vessel comprising a second aqueous solution having pH of 6.0-8.5; and (h) repeating steps (b)-(g) 2-15 times, except in step (d) of each cycle with a sample vessel comprising a new sample, whereby the analyte concentrations of multiple samples are determined. The sample vessel in the repeated cycle is preferably a new sample vessel.

The method uses the same probe, the same washing solution, and the same reagents in all cycles of reaction. However, a fresh reagent solution can also be used in different cycles.

In step (a) of the present method, a probe that has a small tip for binding an analyte is obtained. The tip has a smaller surface area with a diameter≤5 mm, preferably ≤2 mm or ≤1 mm. The small surface of the probe tip endows it with several advantages. In a solid phase immunoassays, having a small surface area is advantageous because it has less non-specific binding and thus produces a lower background signal. Further, the reagent or sample carry over on the probe tip is extremely small due to the small surface area of the tip. This feature makes the probe tip easy to wash and results in negligible contamination in the wash solution since the wash solution has a larger volume. Another aspect of the small surface area of the probe tip is that it has small binding capacity. Consequently, when the probe tip is immersed in a reagent solution, the binding of the reagent does not consume a significant amount of the reagent. The reagent concentration is effectively unchanged. Negligible contamination of the wash solution and small consumption of the reagents enable the reagents and the wash solution to be re-used many times, for example, 3-10 times, 3-15 times, or 3-20 times.

Methods to immobilize a hapten to the solid phase (the sensing surface of the probe tip) are common in immunochemistry and involve formation of covalent, hydrophobic or electrostatic bonds between the solid phase and a hapten. For example, a hapten can be conjugated to a carrier protein and the hapten-protein is immobilized either by adsorption to the solid surface or by covalently binding to aminopropylsilane coated on the solid surface.

In step (b) of the method, the probe tip is dipped into a dual antibody vessel containing a dual antibody solution. The dual antibody solution contains an anti-hapten antibody covalently linked to a capture antibody, wherein the capture antibody is a first antibody against the analyte. Alternatively, the dual antibody solution contains a bi-specific antibody that simultaneously bind to the hapten and the analyte.

In one embodiment, the anti-hapten antibody and the capture antibody are directly linked to each other without a linker.

In a preferred embodiment, the anti-hapten antibody and the capture antibody are both covalently linked to a polymer, which serves as a linker or spacer. The polymer in general has a molecular weight of 1,000 to 500,000 Daltons. The polymer can be a polysaccharide (e.g., dextran, amylose), a dendrimer, or a polyethylene glycol. In one preferred embodiment, the polymer is FICOLL® (copolymers of sucrose and epichlorohydrin).

In step (c), the probe is dipped in a first wash vessel (a baseline vessel which also serves the function of washing the probe) comprising a first aqueous solution preferably having pH of 6.0-8.5 for a first period of time (e.g., 5 seconds to 5 minutes, 10 seconds to 2 minutes, or 30 seconds to 1 minute), to determine a baseline interferometry pattern of the probe tip. The baseline vessel contains an aqueous solution such as water or a buffer having pH between 6.0 to 8.5. Preferably, the aqueous solution contains 1-10 mM or 1-100 mM of phosphate buffer, tris buffer, citrate buffer or other buffer suitable for pH between 6.0-8.5.

In step (d) of the method, the probe tip is dipped into a sample vessel (or a sample chamber or a sample well) containing a liquid sample having the analyte for a second period of time (e.g., 5 seconds to 5 minutes, 10 seconds to 2 minutes, or 30 seconds to 1 minute), to determine a second interferometry pattern of the immunocomplex formed at the probe tip.

In step (e), the analyte concentration in the sample is quantitated by determining the interferometry phase shift between the second interferometry pattern and the baseline interferometry pattern, and quantitating the wavelength phase shift against a calibration curve to determine the analyte concentration. The phase shift can be monitored either kinetically or determined by the difference between starting time point (T0) and end time point (T1) (see FIG. 3B).

In step (f), the probe is regenerated by employing a denaturing condition that dissociates the immune complexes bound to the capture antibody on a solid phase. In general, an acid or an acidic buffer having pH about 1 to about 4 is effective to regenerate the antibody probe of the present invention. For example, hydrochloric acid, sulfuric acid, nitric acid, acetic acid can be used to regenerate the probe. The regeneration procedures can be one single acidic treatment, followed by neutralization. For example, a single pH 1-3, or pH 1.5-2.5 (e.g., pH 2) exposure ranging from 10 seconds to 2 minutes is effective. The regeneration procedures can also be a "pulse" regeneration step, where the probe is exposed to 2-5 cycles (e.g. 3 cycles) of a short pH treatment (e.g., 10-20 seconds), followed by neutralization at pH 6.5-8.0 (e.g., 10-20 seconds).

In step (g), after regeneration, the probe tip is dipped in a second wash vessel comprising a second aqueous solution having pH of 6.0-8.5 to neutralize the probe.

After regeneration and wash of the probe, steps of (b)-(g) are repeated with a different sample in a subsequent cycle, for 1-10, 1-20, 1-25, 3-20, 5-10, 5-20, 5-25, or 5-30 times, with the same probe and the same reagents.

In one embodiment, the reaction is accelerated by agitating or mixing the solution in the vessel. For example, a flow such as a lateral flow or an orbital flow of the solution across the probe tip can be induced in one or more reaction vessels, including sample vessel, reagent vessel, wash vessels, and regeneration vessel, to accelerates the binding reactions, disassociation. For example, the reaction vessels can be mounted on an orbital shaker and the orbital shaker is rotated at a speed at least 50 rpm, preferably at least 200 rpm or at least 500 rpm, such as 50-200 or 500-1,500 rpm. Additionally, the probe tip can be moved up and down and perpendicular to the plane of the orbital flow, at a speed of 0.01 to 10 mm/second, in order to induce additional mixing of the solution above and below the probe tip.

Second Embodiment—Kinetics

Figure 5:
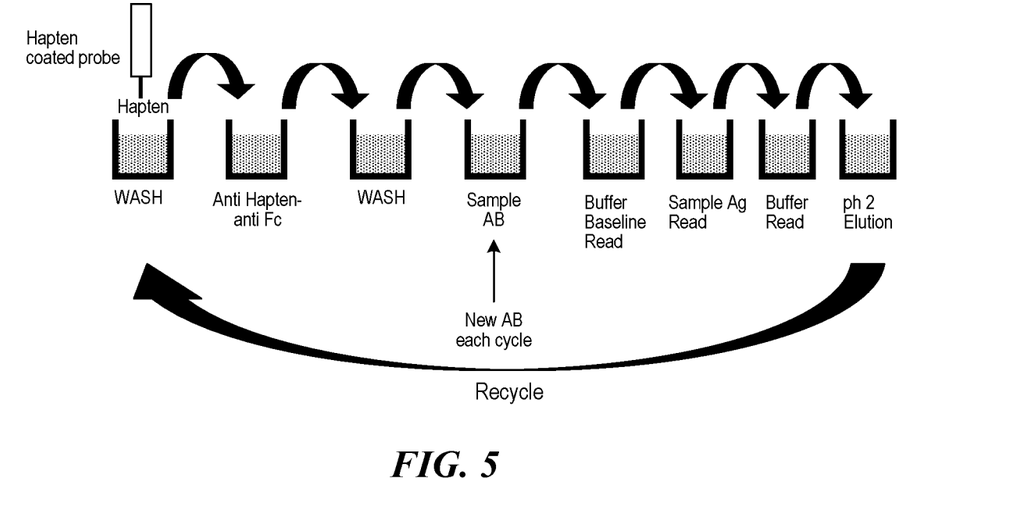
FIG. 5 illustrates the second embodiment of the invention for antigen-antibody binding kinetics, where the anti-hapten antibody is covalently linked to a capture antibody. (Ag=antigen, AB=antibody)

The second embodiment of the invention measures the binding kinetics of a sample antibody to a sample antigen in multiple samples each comprising a sample antibody. This embodiment is illustrated in FIG. 5.

The method is useful for measuring on rate and off rate of an antibody to an antigen, and to determine the antibody affinity to the antigen. The method comprises the steps of: (a) obtaining a probe having a hapten immobilized on the tip of the probe, wherein the diameter of the tip surface is ≤5 mm; (b) dipping the probe tip in a dual antibody vessel containing a dual antibody solution comprising an anti-hapten antibody covalently linked to a first antibody, wherein the first antibody is an antibody against the Fc portion of a sample antibody; (c) dipping the probe tip into an antibody sample vessel containing the sample antibody, to bind the sample antibody to the probe, wherein the sample antibody binds specifically to a sample antigen; (d) dipping the probe tip in a first wash vessel comprising a first aqueous solution for a first period of time to determine a baseline interferometry pattern of the probe tip; (e) dipping the probe tip into an antigen sample vessel comprising the sample antigen for a second period of time to bind the sample antigen to the probe and to determine a second interferometry pattern; (f) calculating the interferometry phase shift between the second interferometry pattern and the baseline interferometry pattern to determine the binding kinetics of the sample antibody and the sample antigen; (g) dipping the probe tip into a second wash vessel comprising a second aqueous solution to measure a third interferometry pattern; (h) calculating the interferometry phase shift between the third interferometry pattern and the second interferometry pattern to determine the disassociation kinetics of the sample antibody and the sample antigen; (i) dipping the probe tip in an acidic solution having pH about 1.0-4.0 to elute remaining immunocomplex on the probe tip; (j) dipping the probe tip in a third wash vessel comprising a third aqueous solution having pH of 6.0-8.5; and (k) repeating steps (b)-(j) 3-15 times, except in step (c) of each cycle with an antibody sample vessel comprising a new sample antibody, whereby the binding kinetics of multiple sample antibodies are determined.

The details of each step are similar to those of a corresponding similar step, if any, described above in the first embodiment.

An example of the first antibody in step (b) is an anti-mouse IgG antibody, and the sample antibody is a mouse antibody against a sample antigen.

Step (e) binds the sample antigen to the sample antibody on the probe. Step (f) calculates the association rate (binding) of the sample antibody to the sample antigen. Step (g) dissociates the sample antigen from the sample antibody on the probe by dipping the probes in a second wash solution that does not contain any sample antigen. Step (h) calculates the disassociation rate of the sample antibody to the sample antigen.

Third Embodiment—Streptavidin-Quantitation

In a third and fourth embodiment, anti-hapten and streptavidin conjugate is used instead of the dual antibody used in the first two embodiments.

In one embodiment, the anti-hapten antibody and streptavidin are directly linked to each other without a linker.

In a preferred embodiment, the anti-hapten antibody and streptavidin are both covalently linked to a polymer, which serves as a linker or spacer. The polymer in general has a molecular weight of 1,000 to 500,000 Daltons. The polymer can be a polysaccharide (e.g., dextran, amylose), a dendrimer, or a polyethylene glycol. In one preferred embodiment, the polymer is FICOLL® (copolymers of sucrose and epichlorohydrin).

There are a several applications of using the streptavidin-coated probe for detection of biotin. The initial step involves incorporating biotin into bio-molecules. There are many commercially available biotin analogues designed for coupling to primary and secondary amines, sulfhydryls, carboxyls and carbohydrate moieties of bio-molecules. Most of the coupling procedures are now considered standard. The most common analogue is biotin-NHS ester for labeling to primary amines on protein. Recently, recombinant labeling methods were developed. AviTag™ is a fusion peptide that is incorporated into a recombinant protein during expression. A biotin ligase then inserts biotin on a lysine residue in the fusion peptide.

One application of the streptavidin probe is quantification of biotin tagged protein, typically employed in monitoring recombinant protein production and purification.

Figure 6:
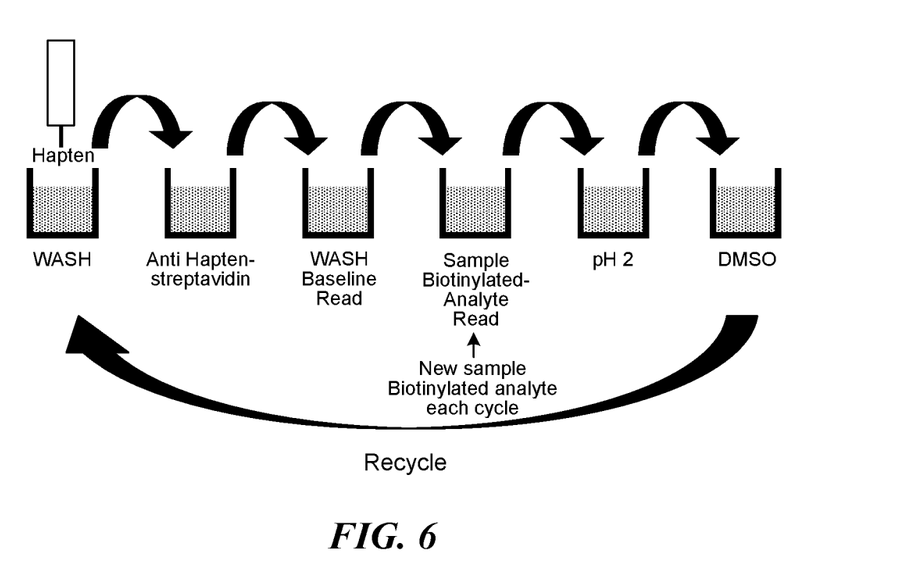
FIG. 6 illustrates the third embodiment of the invention for quantitation of a biotinylated analyte, where the anti-hapten antibody is covalently linked to streptavidin.

In the third embodiment, the method detects a biotinylated analyte in multiple samples. This embodiment is illustrated in FIG. 6 with a biotinylated analyte in the sample to be quantitated. The method comprises the steps of: (a) obtaining a probe having a hapten immobilized on the tip of the probe, wherein the diameter of the tip surface is ≤5 mm; (b) dipping the probe tip in a solution comprising an anti-hapten antibody covalently linked to streptavidin; (c) dipping the probe tip in a first wash vessel comprising a first aqueous solution for a first period of time to determine a baseline interferometry pattern of the probe tip; (d) dipping the probe tip into a sample vessel containing a liquid sample having a biotinylated analyte for a second period of time to determine a second interferometry pattern of the complex formed at the probe tip; (e) determining the biotinylated analyte concentration in the sample by measuring the interferometry phase shift between the second interferometry pattern and the baseline interferometry pattern, and quantitating the phase shift against a calibration curve; (f) dipping the probe tip in an acidic solution having pH about 1.0-4.0 and then in a DMSO solution to elute the complex from the probe tip; (g) dipping the probe tip in a second wash vessel comprising a second aqueous solution having pH of 6.0-8.5; and (h) repeating steps to (b)-(g) 3-15 times, except in step (d) of each cycle with a sample vessel comprising a new sample, whereby the biotinylated-analytes in multiple liquid samples are detected.

The details of each step are similar to those of a corresponding similar step, if any, described above in the first embodiment.

Using a streptavidin conjugate demands more stringent elution conditions, and a dimethyl sulfoxide (DMSO) solution is used as a second elution agent after the acidic elution. In general, an aqueous solution (water or a buffer such as PBS) of DMSO is used with DMSO in an amount of 20-85%, 30-85%, or 40-80% by weight.

Fourth Embodiment—Streptavidin-Kinetics

Another application of streptavidin is obtaining the affinity constants for binding pairs. The most common is optimization of bio-therapeutic antibodies. Affinity constants are typically determined by initially binding a biotinylated antigen to the streptavidin probe followed by immersing the probe in a sample containing a known concentration of antibody to measure the association rate. The probe is then transferred to a buffer sample containing no antibody to measure the disassociation rate of the immune complex. The streptavidin probe with regeneration protocol is most useful in affinity maturation programs to further enhance antibody affinity by generating random mutations in the CDR region. Many antibody variants are produced requiring a rapid, cost effective means to characterize their affinities.

Figure 7:
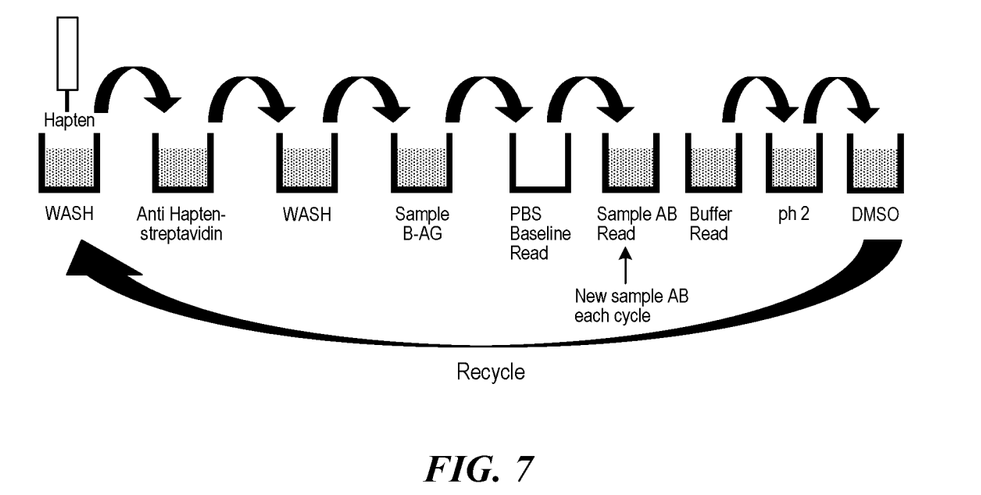
FIG. 7 illustrates the fourth embodiment of the invention for binding kinetics of a binding pair, where the anti-hapten antibody is covalently linked to streptavidin. The binding pair is antibody and biotinylated antigen.
Figure 8:
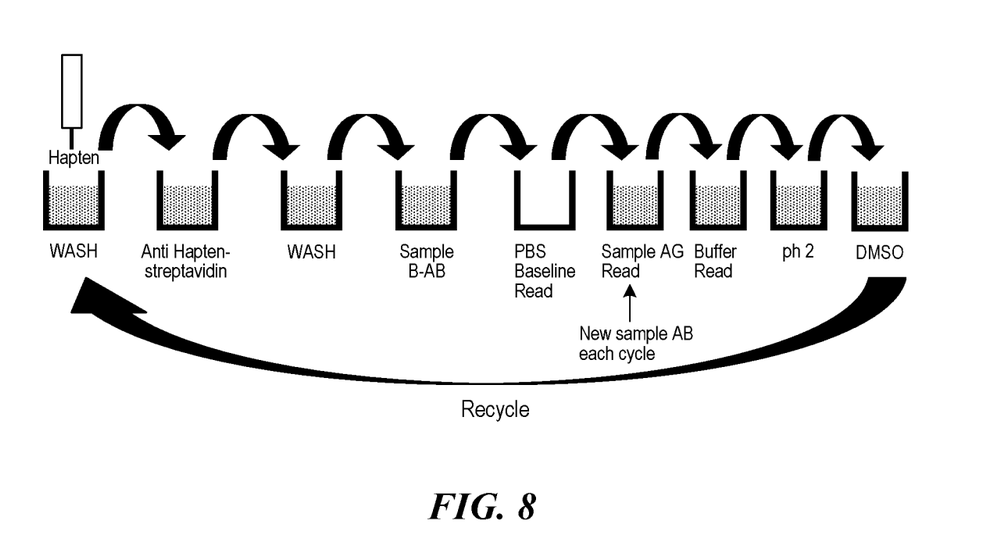
FIG. 8 also illustrates the fourth embodiment of the invention for binding kinetics of a binding pair, where the anti-hapten antibody is covalently linked to streptavidin. The binding pair of this figure is antigen and biotinylated antibody.

In the fourth embodiment of the invention, the method measures the binding kinetics of a binding pair. Examples of binding pairs include, but not limited to, an antigen and an antibody against the antigen, a ligand and its receptor, complementary strands of nucleic acids, biotin and avidin, biotin and streptavidin, lectin and carbohydrates. The fourth embodiment is illustrated by FIGS. 7 and 8. In FIG. 7, the first member of the binding pair is an antigen, and the second member of the binding pair is an antibody. In FIG. 8, the first member of the binding pair is an antibody, and the second member of the binding pair is an antigen.

The method comprises the steps of: (a) obtaining a probe having a hapten immobilized on the tip of the probe, wherein the diameter of the tip surface is ≤5 mm; (b) dipping the probe tip in a solution comprising an anti-hapten antibody covalently linked to streptavidin; (c) dipping the probe tip into a first sample vessel comprising a biotinylated first member of a binding pair;

(d) dipping the probe tip in a first wash vessel comprising a first aqueous solution for a first period of time to determine a baseline interferometry pattern of the probe tip; (e) dipping the probe tip into a second sample vessel comprising the second member of a binding pair for a second period of time to bind the second member of a binding pair to the probe and to determine a second interferometry pattern; (f) calculating the interferometry phase shift between the second interferometry pattern and the baseline interferometry pattern to determine the binding kinetics of the first and the second members of the binding pairs; (g) dipping the probe tip into a second wash vessel comprising a second aqueous solution to measure a third interferometry pattern; (h) calculating the interferometry phase shift between the third interferometry pattern and the second interferometry pattern to determine the disassociation kinetics of the first and the second members of the binding pairs; (i) dipping the probe tip in an elution vessel comprising an acidic solution having pH about 1.0-4.0, and then dipping the probe tip in a DMSO solution to elute remaining immunocomplex on the probe tip; (j) dipping the probe tip in a third wash vessel comprising a third aqueous solution having pH of 6.0-8.5; and (k) repeating steps (b)-(j) 3-15 times, except in step (e) of each cycle with a sample vessel comprising a new second member of the binding pair, whereby the binding kinetics of the first and the second members of the binding pair in multiple samples are determined.

The details of each step are similar to those of a corresponding similar step, if any, described above in the first embodiment or the third embodiment.

In all the methods described above, the reagent vessels are optionally overlaid with a layer of mineral oil to prevent or reduce the evaporation of the solutions in the vessels, which may increase the concentration of the signal antibody conjugate or the amplification conjugate. In general, the solutions in the vessels have a volume of about 50-300 µL, preferably 100-200 µL. The mineral oil layer typically has a volume of 20-80 µL, or 30-50 µL. Mineral oil is commonly used to minimize evaporation and subsequent condensation in PCR sample tubes. The inventor has demonstrated that the probe and immune complexes at the probe tip are not affected by the passage through the mineral oil layer.

Probe Comprising an Immobilized Hapten

The present invention utilizes a probe comprising a hapten immobilized on the tip of the probe, wherein the probe has an aspect ratio of length to width of at least 5 to 1, the diameter of the probe tip surface is ≤5 mm, and the hapten does not dissociate from the probe after an acidic treatment; i.e., no more than 15%, preferably no more than 10% or 5% of the hapten is dissociated from the probe after 1-20 cycles of the acid treatment. The acid treatment is typically performed by dipping the probe in a low pH buffer (pH 1-4, or 1-3, or 1.5-2.5) for 10 seconds to 2 minutes. The DMSO treatment is typically performed by dipping the probe in a DMSO solution for 10 seconds to 2 minutes.

The invention is illustrated further by the following examples that are not to be construed as limiting the invention in scope to the specific procedures described in them.

EXAMPLES

Example 1: Preparation of Hapten Coated Probes

A variety of hapten/anti hapten pairs may be used in this invention. Fluorescein and digoxiginnen are useful haptens for this invention because their analogues for labeling and their antibodies are readily available. The first step is to link the hapten to a polymer, typically a protein such as BSA (bovine serum albumin). The protein is for subsequent immobilization to the probe surface. For example, fluorescein-NHS ester (Invitrogen) or digoxigennin-NHS ester (ATT Bioquest) was reacted with BSA at a molar coupling ratio of 15 to 1 in PBS pH 7.4 for 1 hour, followed by purification on a PD10 column (GE Healthcare).

A probe shown in FIG. 2 was prepared as follows. Both ends of glass (refractive index 2.0) rods with 20 mm in length and 1 mm in diameter were polished to mirror surfaces using an optical polishing machine. After the rods were washed and cleaned in purified water, they were arrayed in a fixture that is then loaded into an ion-beam-assisted physical vapor deposition (PVD) machine. In the PVD machine, an electron beam is used to bombard and vaporize a target material to be coated onto the surface; an ion beam is then applied to deposit the vapor on to the surface to form a thin film layer. The glass rods were coated first with a 940-nm $MgF_2$ layer, followed by a 5-nm $SiO_2$ layer. After the surface was coated with the $MgF_2/SiO_2$ layers, the rods were place in a chemical vapor deposition (CVD) machine to coat a thin layer of aminopropylsilane (APS) that is typically 1-2 nm in thickness.

The probe tip was then immersed in a solution of either fluorescein-BSA or digoxiginnen-BSA, 30 μg/ml in PBS at pH 7.4. After allowing the BSA to adsorb to the probe for 10 minutes, the probe tip was washed in PBS.

Example 2: Dual Antibody Anti-Hapten and Anti-Fc Preparation

Dual antibody conjugate was prepared for an assay for detecting IgG. A conjugate of anti-hapten and anti-Fc was prepared as follows. 2 mgs of amino FICOLL® (Skold Technolgy) in PBS, pH 7.4, was reacted with SPDP (ThermoFisher) at a molar coupling ratio of 10 to 1 for 1 hour followed by an overnight dialysis. De-protection of the thiols occurred by adding 30 μl of DTT (ThermoFisher). After 1 hour, the material was purified on a PD10 column.

2 mgs of anti-hapten, either anti-fluorescein (Jackson Immunoresearch) or anti digoxigennin (Thermo Fisher), were mixed with 2 mgs anti-Fc (Jackson Immunoresearch) and reacted with SMCC (ThermoFisher) at a molar coupling ratio of 15 to 1 for 1 hour followed by purification on a PD10 column.

The SMMC labeled antibody mixture was reacted with the thiolated FICOLL® overnight, then it was purified on a Sepharose CL-6B column (GE Healthcare), to prepare FICOLL® linked with anti-fluorescein and anti-Fc.

Example 3: Preparation of Anti-Hapten Linked to Streptavidin 2 mg of amino-FICOLL® (Skold Technolgy) in PBS, pH 7.4, was reacted with SPDP (ThermoFisher) at a molar coupling ratio of 10 to 1 for 1 hour followed by an overnight dialysis. De-protection of the thiols occurred by adding 30 μl of DTT (ThermoFisher). After 1 hour, the material was purified on a PD10

2 mg of anti-fluorescein was reacted with SMCC at a molar coupling ratio of 15 to 1 for 1 hour, followed by PD10 column purification. In a parallel reaction, 4 mgs of streptavidin (Prozyme) was reacted with SMCC at a molar coupling ratio of 15 to 1, then purified on a PD 10 column, The SMCC-anti fluorescein, SMCC-streptavidin, and thiolated-FICOLL® were mixed together and after reacting overnight, purified in a Sepharose CL-6B column.

Example 4: Assay for IgG (Fc)

FIG. 4 diagrams the protocol for the assay of IgG (Fc) and the sequence of probe transfers through micowells containing IgG (Fc) samples and various reagents. Initially a probe with fluorescein (Hapten)-BSA coated on the tip is immersed in a reagent containing a dual antibody conjugate of anti-fluorescein linked to anti-Murine IgG (Fc) through FICOLL® (Example 2). After a binding step and probe wash step, the probe is immersed in a sample of murine IgG. The binding of murine IgG to the probe is monitored by the interference shift versus time. After the binding step the probe is immersed in a denaturing reagent, in this case 10 mM glycine/HCl buffer pH 2.0. The low pH disassociates the immune complex from the probe surface while leaving fluorescein-BSA free on the probe for a subsequent binding. The probe is then cycled back to the anti F-anti murine IgG (Fc) reagent for a fresh coating of antibody followed by an assay sequence with another IgG sample.

Table 1 depicts the details of the assay protocol, volumes, incubation times, etc. K Buffer is 0.02% BSA, 0.002% Tween 20, PBS pH 7.4. After regeneration, the probe was recycled to Step 1.

TABLE 1

Assay Protocol (Embodiment 1)

| Step | | Buffer | RPM | Time (sec) | volume (μL/well) |
|---|---|---|---|---|---|
| 1 | Wash | PBS | 1000 | 10 | 350 |
| 2 | anti-F-anti-mouse $F_C$ 100 μg/mL | PBS | 1000 | 180 | 200 |
| 3 | Wash | K buffer | 1000 | 10 | 350 |
| 4 | Wash | K buffer | 1000 | 10 | 350 |
| TEST | IgG or Fc sample | K buffer | 1000 | 120 | 200 |
| Regeneration | Acid | 10 mM Glycine, pH 2.0 | 1000 | 10 | 200 |
| | wash | K buffer | 1000 | 30 | 200 |
| | Acid | 10 mM Glycine, pH 2.0 | 1000 | 10 | 200 |
| | wash | K buffer | 1000 | 30 | 200 |
| | Acid | 10 mM Glycine PH 2.0 | 1000 | 10 | 200 |
| | wash | K buffer | 1000 | 10 | 200 |
| | wash | PBS | 1000 | 30 | 200 |

Figure 9:
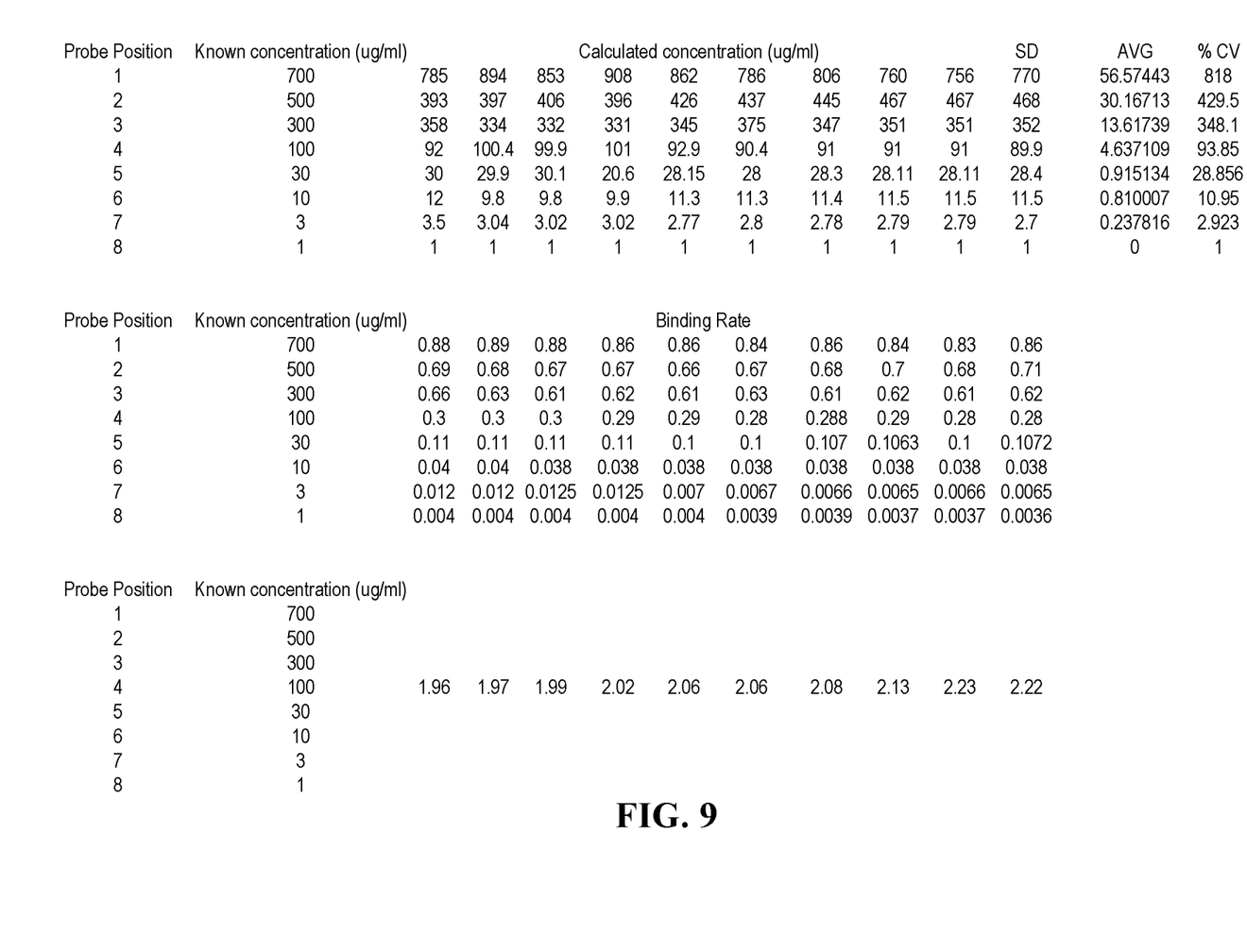
FIG. 9 shows data with multiple levels of murine IgG samples ranging from 1 to 700 µg/ml with 10 regeneration cycles, using the first embodiment of the invention.

For these examples, the probe was held stationary with microwells (1 mm diameter) mounted on an orbital shaker at 1000 rpm creating flow to accelerate binding kinetics. FIG. 9 contains data with multiple levels of murine IgG samples ranging from 1 to 700 μg/ml with 10 regeneration cycles. At each level, the same fluorescein coated probe and the same anti-fluorescein-anti-murine Fc reagent was used.

Table 2 shows data for an assay for human IgG using an anti-fluorescein-anti human IgG (Fc) conjugate following the protocol described in FIG. 4. A total of 23 regeneration cycles were performed with consistent nm shift with IgG samples ranging from 4 to 333 μg/ml.

TABLE 2

Human IgG Assay

| [hIgG] ug/mL: | nm shift (nm) | | | | |
|---|---|---|---|---|---|
| | 4 | 12 | 37 | 111 | 333 |
| 1 | 0.35 | 0.72 | 1.08 | 1.33 | 1.41 |
| 2 | 0.30 | 0.71 | 1.08 | 1.34 | 1.44 |
| 3 | 0.27 | 0.70 | 1.10 | 1.32 | 1.39 |
| 4 | 0.30 | 0.71 | 1.08 | 1.34 | 1.39 |
| 5 | 0.28 | 0.71 | 1.09 | 1.33 | 1.43 |
| 6 | 0.28 | 0.71 | 1.08 | 1.34 | 1.42 |
| 7 | 0.27 | 0.71 | 1.09 | 1.34 | 1.40 |
| 8 | 0.28 | 0.70 | 1.11 | 1.34 | 1.42 |
| 9 | 0.27 | 0.71 | 1.09 | 1.35 | 1.40 |
| 10 | 0.29 | 0.69 | 1.09 | 1.35 | 1.40 |
| 11 | 0.27 | 0.70 | 1.10 | 1.33 | 1.41 |
| 12 | 0.27 | 0.69 | 1.09 | 1.33 | 1.41 |
| 13 | 0.27 | 0.70 | 1.10 | 1.34 | 1.43 |
| 14 | 0.26 | 0.69 | 1.09 | 1.32 | 1.41 |
| 15 | 0.27 | 0.69 | 1.09 | 1.33 | 1.42 |
| 16 | 0.26 | 0.68 | 1.08 | 1.33 | 1.41 |
| 17 | 0.25 | 0.68 | 1.08 | 1.32 | 1.38 |
| 18 | 0.25 | 0.67 | 1.08 | 1.32 | 1.41 |
| 19 | 0.24 | 0.66 | 1.09 | 1.31 | 1.44 |
| 20 | 0.25 | 0.67 | 1.11 | 1.33 | 1.43 |
| 21 | 0.24 | 0.68 | 1.09 | 1.33 | 1.41 |
| 22 | 0.25 | 0.67 | 1.07 | 1.31 | 1.37 |
| 23 | 0.21 | 0.67 | 1.10 | 1.32 | 1.43 |
| Average | 0.27 | 0.69 | 1.10 | 1.33 | 1.41 |
| Stdev | 0.03 | 0.02 | 0.01 | 0.01 | 0.02 |
| CV % | 10.0% | 2.4% | 1.0% | 0.9% | 1.3% |

Example 5: Assay for Biotin-Tagged Protein

FIG. 6 diagrams the transfer sequence for a fluorescein-coated probe through microwells containing anti fluorescein-streptavidin conjugate reagent, followed by immersion in a biotin-tagged IgG sample. Due to the high affinity of streptavidin, 2 denaturation steps were required to release the immune complex from the probe. The first denaturation was 10 mM glycine/HCl pH 2.0, followed by DMSO (typically 20-40% in PBS).

Table 3 shows the details of the assay protocol, volumes, incubation times, etc.

TABLE 3

Protocol with Streptavidin probe, biotin-mouse IgG sample

| | Step | Buffer | RPM | Time (sec) | volume (µL/well) |
|---|---|---|---|---|---|
| 1 | Baseline | PBS | 1000 | 60 | 200 |
| 2 | anti-F-SA 100 µg/mL | PBS | 1000 | 180 | 200 |
| 3 | Wash | K Buffer | 1000 | 10 | 350 |
| 4 | Wash | K Buffer | 1000 | 10 | 350 |
| TEST | Biotin-mIgG 1-10 µg/mL | K buffer | 1000 | 120 | 200 |
| Regeneration | Acid | 10 mM Glycine, pH 2.0 | 1000 | 10 | 200 |
| | DMSO wash | 30% DMSO in PBS PBS | 1000 1000 | 10 30 | 200 200 |
| | Acid | 10 mM Glycine, pH 2.0 | 1000 | 10 | 200 |
| | DMSO wash | 30% DMSO in PBS PBS | 1000 1000 | 10 30 | 200 200 |
| | Acid | 10 mM Glycine, pH 2.0 | 1000 | 10 | 200 |
| | DMSO wash | 30% DMSO in PBS PBS | 1000 1000 | 10 30 | 200 200 |

Table 4 shows the results of 15 regeneration cycles of biotin IgG samples at 10 µg/ml with the same fluorescein coated probe and the anti-fluorescein-streptavidin conjugate reagent. Three probes were tested in replicate showing consistent results from probe to probe.

TABLE 4

Biotin-IgG samples

| # of regeneration | Δ nm at 120 sec | | |
|---|---|---|---|
| | 1 | 2 | 3 |
| 1 | 0.645 | 0.571 | 0.654 |
| 2 | 0.662 | 0.585 | 0.647 |
| 3 | 0.643 | 0.551 | 0.639 |
| 4 | 0.681 | 0.595 | 0.673 |
| 5 | 0.67 | 0.563 | 0.659 |
| 6 | 0.694 | 0.6 | 0.678 |
| 7 | 0.663 | 0.569 | 0.659 |
| 8 | 0.694 | 0.598 | 0.672 |
| 9 | 0.708 | 0.611 | 0.686 |
| 10 | 0.711 | 0.617 | 0.669 |
| 11 | 0.702 | 0.631 | 0.679 |
| 12 | 0.695 | 0.605 | 0.66 |
| 13 | 0.678 | 0.603 | 0.645 |
| 14 | 0.67 | 0.594 | 0.652 |
| 15 | 0.651 | 0.587 | 0.65 |
| AVERAGE | 0.678 | 0.592 | 0.661 |
| ST. DEV | 0.022 | 0.022 | 0.014 |
| % CV | 3.31% | 3.63% | 2.12% |

Example 6: Kinetics with Anti-Murine Fc Probe

The protocol of this example is illustrated by FIG. 5.
Materials:
Probe: F-BSA
Dual Antibody: Anti F-anti murine Fc
Sample antibody: Anti-CRP, mouse antibody C5 4.9 mg/ml, HyTes
Sample antigen: Recombinant human CRP, Sino Biological Inc.
Wash: PBS or K Buffer (0.02% BSA, 0.002% Tween 20, PBS pH 7.4)
Regeneration Buffer: 10 mM Glycine pH 2.0
The details of the assay protocol are shown in Table 5.

TABLE 5

Anti MuFc Probe, Mu antiCRP/CRP Kinetics

| Step | Name | Time (sec) | RPM | Volume (µl/well) |
|---|---|---|---|---|
| 1 | Wash | 60 | 1000 | 250 |
| 2 | Anti F-anti Fc | 180 | 500 | 200 |
| 3 | Wash | 60 | 1000 | 250 |
| 4 | Sample anti-CRP, 5 µg/ml | 180 | 1000 | 250 |
| 5 | Baseline | 30 | 1000 | 250 |
| 6 | Sample CRP (100 nM, 50 nM, 25 nM, 12.5 nM, 6 nM, and 3 nM) -Association | 300 | 1000 | 250 |
| 7 | Buffer (no CRP) Disassociation | 600 | 1000 | 250 |
| 8 | 10 mM Glycine, pH 2.0 | 5 | 1000 | 250 |
| 9 | PBS | 5 | 1000 | 250 |
| 10 | 10 mM Glycine, pH 2.0 | 5 | 1000 | 250 |
| 11 | PBS | 5 | 1000 | 250 |
| 12 | 10 mM Glycine, pH 2.0 | 5 | 1000 | 250 |
| 13 | PBS | 5 | 1000 | 250 |

Figure 10:
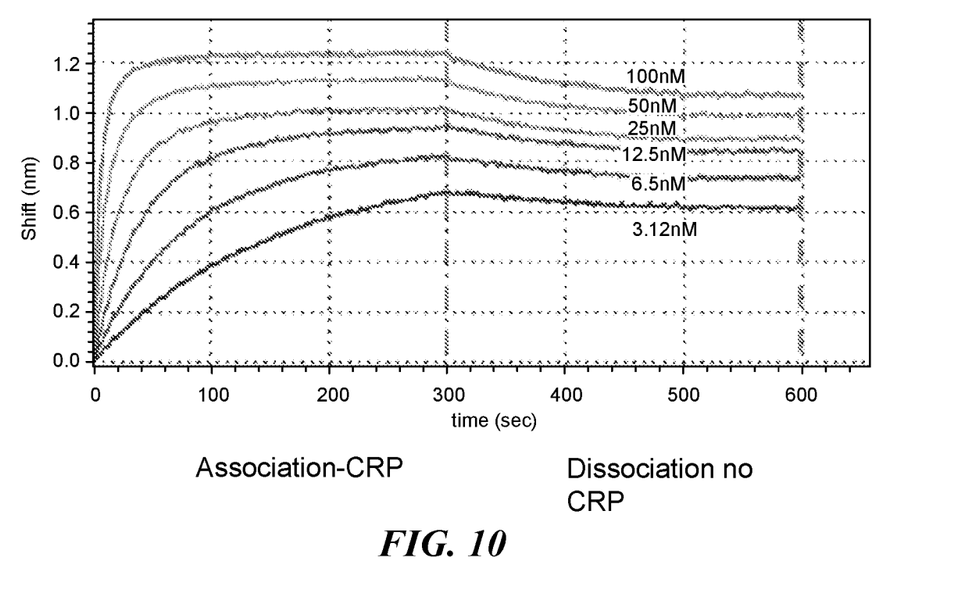
FIG. 10 shows the interference patterns of binding kinetics of CRP and anti-CRP with anti-murine Fc coated probe.

The nm shift in interference pattern is shown in FIG. 10. The first 300 seconds show association of anti-CRP and CRP. The second 300 seconds show disassociation of anti-CRP and CRP in buffer.

The results of on rate, off rate, and $K_D$ are shown in Table 6. $K_D$=0.36±0.1 nM.

TABLE 6

Anti MuFc Probe, Mu antiCRP/CRP Kinetics

| | $k_{off}$ | $k_{on}$ | $K_D$ |
|---|---|---|---|
| Assay 1 | 1.56E−04 | 3.40E+05 | 0.46 nM |
| Assay 2 | 1.08E−04 | 3.26E+05 | 0.33 nM |
| Assay 3 | 1.36E−04 | 3.00E+05 | 0.46 nM |
| Assay 4 | 1.44E−04 | 3.19E+05 | 0.45 nM |
| Assay 5 | 6.60E−05 | 3.04E+05 | 0.22 nM |
| Assay 6 | 5.70E−05 | 2.98E+05 | 0.19 nM |
| Assay 7 | 1.36E−04 | 3.00E+05 | 0.46 nM |
| Assay 8 | 9.93E−05 | 2.68E+05 | 0.37 nM |
| Assay 9 | 8.90E−05 | 2.60E+05 | 0.34 nM |

Example 7: Kinetics with Streptavidin Probe

This protocol of this example is illustrated by FIG. 8.

Materials:

Probe: F-BSA

Antibody-streptavidin: Anti F-Streptavidin

Sample antibody: Biotin-Anti-His Monoclonal antibody (Biospacific)

Sample antigen: His-IL2r, Sino Biologic

Wash: PBS or K Buffer (0.02% BSA, 0.002% Tween 20, PBS pH 7.4)

Regeneration Buffer: 10 mM Glycine pH 2.0 and 75% DMSO in PBS

The details of the assay protocol are shown in Table 7.

TABLE 7

Streptavidin Probe: Anti His-His-IL2r Kinetic Protocol

| | | Reagent | Time (sec) | RPM | Volume (µL/well) |
|---|---|---|---|---|---|
| 1 | Wash | PBS, BSA, Tween-20 | 60 | 1000 rpm | 300 |
| 2 | Activation | 25 ug/mL anti-Flourescein streptavidin | 300 | | 250 |
| 3 | Wash | PBS, BSA, Tween-20 | 30 | | 300 |
| 4 | Wash | PBS, BSA, Tween-20 | 30 | | 300 |
| 5 | Load | 10 µg/mL Biotin-anti-His | 300 | | 250 |
| 6 | Baseline | PBS, BSA, Tween-20 | 30 | | 300 |
| Test | Association | 0-245 nM IL2r-His | 5 | | 250 |
| | Disassociation | PBS, BSA, Tween-20 | 5 | | 300 |
| | Regeneration | 10 mM Glycine pH 2 | 5 | | 300 |
| | | 75% DMSO in 1x PBS | 5 | | 300 |
| | | 1x PBS, BSA, Tween-20 | 5 | | 300 |
| | | 10 mM Glycine pH 2 | 5 | | 300 |
| | | 75% DMSO in 1x PBS | 5 | | 300 |
| | | PBS, BSA, Tween-20 | 5 | | 300 |
| | | 10 mM Glycine pH 2 | 5 | | 300 |
| | | 75% DMSO in 1x PBS | 5 | | 300 |
| | | PBS, BSA, Tween-20 | 5 | | 300 |

Figure 11:
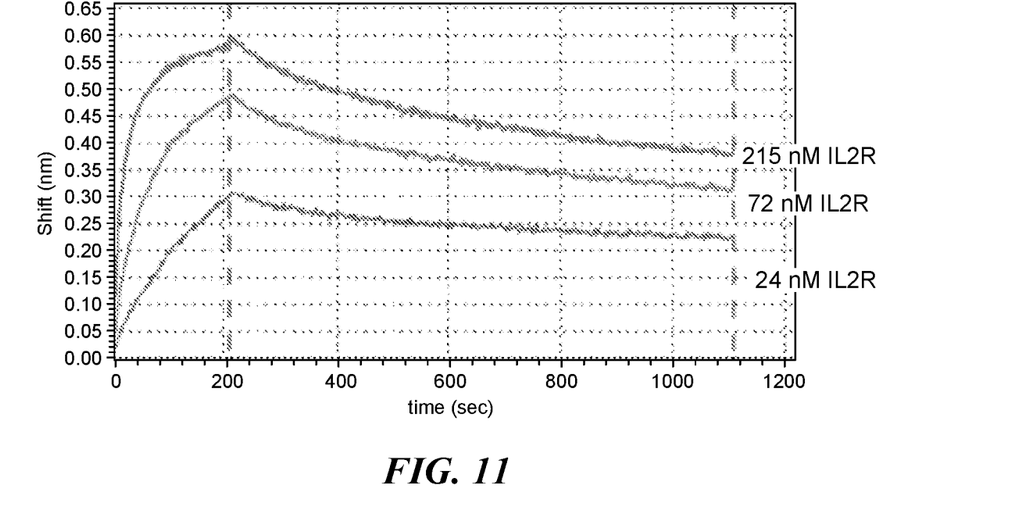
FIG. 11 shows the interference patterns of binding kinetics of biotin-anti-His antibody and His-IL2r, with streptavidin coated probe.

The nm shift in interference pattern is shown in FIG. 11. The first 200 seconds show association of biotin-anti-His with IL2r-His. The next 900 seconds show disassociation of anti-biotin-anti-His and IL2r-His in buffer.

The results of on rate, off rate, and $K_D$ are shown in Table 8.

TABLE 8

Streptavidin Probe: Anti His-His-IL2r Kinetic Results

| Run | koff(1/s) | kon(1/Ms) | KD(M) |
|---|---|---|---|
| Assay 1 | 8.81E−04 | 1.63E+05 | 5.42E−09 |
| Assay 2 | 1.36E−03 | 1.90E+05 | 7.18E−09 |
| Assay 3 | 1.12E−03 | 2.13E+05 | 5.25E−09 |
| Assay 4 | 1.53E−03 | 2.28E+05 | 6.72E−09 |
| Assay 5 | 1.63E−03 | 2.21E+05 | 7.36E−09 |
| Assay 6 | 7.01E−04 | 2.47E+05 | 2.84E−09 |
| Assay 7 | 9.61E−04 | 2.59E+05 | 3.71E−09 |
| Assay 8 | 1.26E−03 | 2.61E+05 | 4.84E−09 |
| Assay 9 | 1.49E−03 | 2.44E+05 | 6.13E−09 |
| Assay 10 | 1.68E−03 | 2.58E+05 | 6.51E−09 |
| Assay 11 | 2.22E−03 | 2.50E+05 | 8.89E−09 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To to particularly point out and distinctly claim the subject matter regarded as invention, the following claims conclude this specification.

What is claimed is:

1. A method of detecting an analyte in multiple liquid samples comprising an analyte, comprising the steps of:

(a) obtaining a probe having a hapten immobilized on the tip of the probe, wherein the diameter of the tip surface is ≤5 mm;

(b) dipping the probe tip in a dual antibody solution comprising an anti-hapten antibody covalently linked to a capture antibody, wherein the capture antibody is an antibody against the analyte;

(c) dipping the probe tip in a first wash vessel comprising a first aqueous solution having pH of 6.0-8.5 for a first period of time to determine a baseline interferometry pattern of the probe tip;

(d) dipping the probe tip into a sample vessel containing a liquid sample having the analyte for a second period of time to determine a second interferometry pattern of the immunocomplex formed at the probe tip;

(e) determining the analyte concentration in the sample by measuring the interferometry phase shift between the second interferometry pattern and the baseline interferometry pattern, and quantitating the phase shift against a calibration curve;

(f) dipping the probe tip in an elution vessel comprising an acidic solution having pH about 1.0-4.0 to elute the immunocomplex from the probe tip;

(g) dipping the probe tip in a second wash vessel comprising a second aqueous solution having pH of 6.0-8.5, and (h) repeating steps (b)-(g) 3-15 times, except in step (d) of each cycle with a vessel comprising a new sample, whereby the analyte concentrations of multiple samples are determined.

2. A method of measuring the binding kinetics of a sample antibody to a sample antigen in multiple samples each comprising a sample antibody, comprising the steps of:
(a) obtaining a probe having a hapten immobilized on the tip of the probe, wherein the diameter of the tip surface is ≤5 mm;
(b) dipping the probe tip in a dual antibody solution comprising an anti-hapten antibody covalently linked to a first antibody, wherein the first antibody is an antibody against the Fc portion of a sample antibody;
(c) dipping the probe tip into an antibody sample vessel containing the sample antibody, to bind the sample antibody to the probe, wherein the sample antibody binds specifically to a sample antigen;
(d) dipping the probe tip in a first wash vessel comprising a first aqueous solution for a first period of time to determine a baseline interferometry pattern of the probe tip;
(e) dipping the probe tip into an antigen sample vessel comprising the sample antigen for a second period of time to bind the sample antigen to the probe and to determine a second interferometry pattern;
(f) calculating the interferometry phase shift between the second interferometry pattern and the baseline interferometry pattern to determine the binding kinetics of the sample antibody and the sample antigen;
(g) dipping the probe tip into a second wash vessel comprising a second aqueous solution to measure a third interferometry pattern;
(h) calculating the interferometry phase shift between the third interferometry pattern and the second interferometry pattern to determine the disassociation kinetics of the sample antibody and the sample antigen;
(i) dipping the probe tip in an elution vessel comprising an acidic solution having pH about 1.0-4.0 to elute remaining immunocomplex on the probe tip;
(j) dipping the probe tip in a third wash vessel comprising a third aqueous solution having pH of 6.0-8.5; and
(k) repeating steps (b)-(j) 3-15 times, except in step (c) of each cycle with a vessel comprising a new sample antibody, whereby the binding kinetics of multiple sample antibodies are determined.

3. The method of claim 1, wherein the anti-hapten antibody and the capture antibody are both covalently linked to a polymer having a molecular weight of 1,000 to 500,000 Daltons.

4. The method of claim 3, wherein the polymer is a polysaccharide, a dendrimer, or a polyethylene glycol.

5. The method of claim 3, wherein the polymer is copolymers of sucrose and epichlorohydrin.

6. The method of claim 1, wherein the acidic solution has a pH of 1.5-2.5.

7. The method of claim 1, wherein the probe tip is exposed to the acidic solution one time for 10 second to 2 minutes.

8. The method of claim 1, wherein the probe tip is exposed to a pulse treatment of 2-5 cycles of the acidic solution treatment followed by neutralization in a solution for 10-20 seconds.

9. A method of detecting biotinylated analytes in multiple liquid samples, comprising the steps of:
(a) obtaining a probe having a hapten immobilized on the tip of the probe, wherein the diameter of the tip surface is ≤5 mm;
(b) dipping the probe tip in a solution comprising an anti-hapten antibody covalently linked to streptavidin;
(c) dipping the probe tip in a first wash vessel comprising a first aqueous solution for a first period of time to determine a baseline interferometry pattern of the probe tip;
(d) dipping the probe tip into a sample vessel containing a liquid sample having a biotinylated analyte for a second period of time to determine a second interferometry pattern of the complex formed at the probe tip;
(e) determining the biotinylated analyte concentration in the sample by measuring the interferometry phase shift between the second interferometry pattern and the baseline interferometry pattern, and quantitating the phase shift against a calibration curve;
(f) dipping the probe tip in an acidic solution having pH about 1.0-4.0 and then in a DMSO solution to elute the complex from the probe tip;
(g) dipping the probe tip in a second wash vessel comprising a second aqueous solution having pH of 6.0-8.5; and
(h) repeating steps (b)-(g) 3-15 times, except in step (d) of each cycle with a vessel comprising a new sample, whereby the biotinylated-analytes in multiple liquid samples are detected.

10. A method of measuring the binding kinetics of a binding pair, comprising the steps of:
(a) obtaining a probe having a hapten immobilized on the tip of the probe, wherein the diameter of the tip surface is ≤5 mm;
(b) dipping the probe tip in a solution comprising an anti-hapten antibody covalently linked to streptavidin;
(c) dipping the probe tip into a first sample vessel comprising a biotinylated first member of a binding pair;
(d) dipping the probe tip in a first wash vessel comprising a first aqueous solution for a first period of time to determine a baseline interferometry pattern of the probe tip;
(e) dipping the probe tip into a second sample vessel comprising the second member of a binding pair for a second period of time to bind the second member of a binding pair to the probe and to determine a second interferometry pattern;
(f) calculating the interferometry phase shift between the second interferometry pattern and the baseline interferometry pattern to determine the binding kinetics of the first and the second members of the binding pairs;
(g) dipping the probe tip into a second wash vessel comprising a second aqueous solution to measure a third interferometry pattern;
(h) calculating the interferometry phase shift between the third interferometry pattern and the second interferometry pattern to determine the disassociation kinetics of the first and the second members of the binding pairs;
(i) dipping the probe tip in an elution vessel comprising an acidic solution having pH about 1.0-4.0, and then dipping the probe tip in a DMSO solution to elute remaining immunocomplex on the probe tip;
(j) dipping the probe tip in a third wash vessel comprising a third aqueous solution having pH of 6.0-8.5; and
(k) repeating steps (b)-(j) 3-15 times, except in step (e) of each cycle with a vessel comprising a new second member of the binding pair, whereby the binding kinetics of the first and the second members of the binding pair in multiple samples are determined.

11. The method of claim 10, wherein the first member of the binding pair is an antigen, and the second member of the binding pair is an antibody.

12. The method of claim 10, wherein the first member of the binding pair is an antibody, and the second member of the binding pair is an antigen.

13. The method of claim 9, wherein the streptavidin and the anti-hapten antibody are both covalently linked to a polymer having a molecular weight of 1,000 to 500,000 Daltons.

14. The method of claim 13, wherein the polymer is a polysaccharide, a dendrimer, or a polyethylene glycol.

15. The method of claim 13, wherein the polymer is copolymers of sucrose and epichlorohydrin.

16. The method of claim 2, wherein the anti-hapten antibody and the capture antibody are both covalently linked to a polymer having a molecular weight of 1,000 to 500,000 Daltons.

17. The method of claim 16, wherein the polymer is a polysaccharide, a dendrimer, or a polyethylene glycol.

18. The method of claim 16, wherein the polymer is copolymers of sucrose and epichlorohydrin.

19. The method of claim 10, wherein the streptavidin and the anti-hapten antibody are both covalently linked to a polymer having a molecular weight of 1,000 to 500,000 Daltons.

20. The method of claim 19, wherein the polymer is a polysaccharide, a dendrimer, or a polyethylene glycol.

* * * * *